United States Patent [19]

Kummer

[11] Patent Number: Plant 7,105

[45] Date of Patent: Jan. 9, 1990

[54] **MUSHROOM PLANT, *PLEUROTUS OSTREATUS* KUMMERI**

[76] Inventor: David A. Kummer, 7967 Candlewood Dr., Boise, Id. 83709

[21] Appl. No.: 249,553

[22] Filed: Sep. 26, 1988

[51] Int. Cl.[4] ..... A01H 15/00

[52] U.S. Cl. ..... Plt./89

[58] Field of Search ..... Plt./89

*Primary Examiner*—Robert E. Bagwill

[57] ABSTRACT

This novel selection of *Pleurotus ostreatus* exhibites a vigorous growth characteristic which is recognized to be a good growth habit. The morphology of this selection has a desirable color, texture and appearance. The production of this selection is good, with efficiency above 100% in a three flush evaluation.

1 Drawing Sheet

RELATED APPLICATION

This application is a substitute application which claims, in part, subject matter which was disclosed in U.S. Plant patent application Ser. No. 06/615,105, filed May 25, 1984, now abandoned.

BACKGROUND OF THE INVENTION

1. Field of Invention

This invention relates to the selection of a new variety of mushroom plant. Pure cultures of *Pleurotus ostreatus* were reproduced vegetatively for a period of time. A strain which possessed morphological and production characteristics which were unique and desirable was selected for the purpose of this petition.

2. Description of the Prior Art

The carpophore or fruit body of the mushroom culture is identified as a *Pleurotus ostreatus* as described by Smith. "Mushrooms in their Natural Habitats" by Alexander H. Smith, published by Hafner Press in 1949. Fruit bodies of the parent material vegetative selection, were examined by Orson K. Miller, Jr. while in Idaho and identified as a variety of *Pleurotus ostreatus.* This parent material vegetative selection was presented as a patent application filed May 25, 1984 under Ser. No. 615,105 and is now abandoned.

SUMMARY OF THE INVENTION

A vegetative selection culture of *Pleurotus ostreatus* had been developed over a period of serveral years. This vegetative selection which expresses morphological and production characteristics that are unique and desirable, was selected for use as parent material. These characteristics are reproducible both vegetatively and sexually. Haploid basidiospores, arising from a tetrad upon separate basidia, were removed from mature gill tissue of this vegetative selection and mated. This mating of haploid single spore isolates produced a pure strain of this vegetatively selected strain. This strain is identified by the petitioner as *Pleurotus ostreatus* kummeri. The description of *Pleurotus ostreatus* kummeri is as follows:

Carpophore fleshy, soft, stipitate with spores borne on gills; uplifted infundibuliform; with a predominantly central stipe to a lesser degree excentric attached stipe. Predominantly orbicular pileus to a lesser degree lobate of 1 to 8 centimeters in diameter at maturity; incurved, entire margin at first becoming plane to uplifted and undulate to lobed; bicolorus of darker periphery and lighter center; pinhead denigrate to ochraceaus tawny, button becoming brownish terra cotta, at maturity buff to white. Pileus surface is dull, moist, glabrous predominantly smooth becoming regulose toward margin. Lamellae long decurrent; distant at stipe, intermediate lamellulate becoming conferted at pileus margin; moderately broad to narrow; brown to ochraceous tawny to white; margin smooth. Predominantly terete, cylindrical stipe often bulbous if solitary or in groups becoming tapered when caespitose; 1 to 4 centimeters in length and 2 to 15 millimeters in diameter; Basal tomentum absent to scarce; erect to obtuse; predominantly inserted to a lesser degree decumbent; striate above and pubescent below; annulus absent; flesh stuffed. Spores narrowly elliptical, smooth, colorless; spore print white, basidiospore tetrad formation.

Growth habit gregarious and caespitose. Fruiting at 65° F. to 85° F. and 90% to 95% relative humidity and a carbon dioxide concentration of 0.02% to 0.18% and light of 20 1× or more and air movement of 6 FPM and 50 FPM, in a substratum of 50% to 75% moisture. The darker color of the pileus is encouraged with a higher moisture substrate, lower temperature, more light and more air movement.

DETAILED DESCRIPTION OF THE INVENTION

Mature gill tissue of the vegetative selection was placed on a glass microscope slide with a drop of water. A micromanipulator probe tip was placed within the focused field of a microscope at 400× magnification.

The micronanipulator probe was prepared in the following fashion: An 8" length of 3 mm glass rod was heated in a small candle like flame unitl soft in the middle section of the 8" length. With a steady and rapid pulling action the glass rod was stretched and removed from the flame simultaneously. The glass rod was then cut into at the thin middle section with scissors. With proper stretching technique a hook can be established at the end of the probe. The microprobe end was examined under the microscope, then trimmed and re-examined repeatedly until the desirable microprobe was obtained.

The glass slide containing the gill tissue was raised into near focus just below the microprobe tip. A tetrad basidium, containing 4 mature appearing basidisospores which were freely arrayed at the ends of the sterigma, was placed directly under the probe so that one of the basidisopores would contact with the microprobe tip when raised into the field of focus. The basidiospore was brought very near to focus, just under the microprobe tip. The microprobe was manipulated slightly, touching the basidiospore, causing the basidiospore to attach to the microprobe tip. The gill tissue slide was lowered out of the field of focus and removed. A sterile plastic petri dish, 100 mm×15 mm, containing a block of gelled sterile corn starch agar approximately 15 mm×15 mm thick, was placed on the microscope stage with the lid off of the dish. This corn starch agar block was positioned under the microprobe tip and raised up so that the surface of the agar was very near to the focus field. The microprobe was manipulated slightly and brought into contact with the surface of the corn starch agar block. The basidiospore was then transferred to the corn starch agar block. The corn starch agar block was then lowered to remove the microprobe from the surface of the block. The corn starch agar block was again raised into the focus field to confirm the presence of basidiospore on the surface of the block.

The corn starch agar block was prepared in the following fashion. Corn starch agar was developed by the petitioner as an improved nutrient agar for the growth and maintenance of fungi in general and the higher fungi in particular. The formula of Corn Starch Agar or C.S.A. is as follows:

| FORMULA | | |
|---|---|---|
| Ingredients per liter | | |
| Wheat Flour | 2 | grams |
| Brewer's Yeast | 4 | grams |
| Corn Starch | 6 | grams |
| Saccharose | 10 | grams |
| Agar | 16 | grams |

C.S.A. was prepared, sterilized and dispensed, at the depth of about 5 mm, into sterile plastic petri dishes of 100 mm×15 mm in size. After cool down time the gelled C.S.A. was cut into blocks approximately 15 mm×15 mm in size, with a flame sterilized spatula. The C.S.A. blocks were then removed with the sterile tipped spatula and placed in sterile plastic petri dishes 100 mm×15 mm. The C.S.A. block is placed off center within the dish so that the top surface of the C.S.A. remains the top surface after placement. This placement is relative to the procedure in that the lower surface of the C.S.A. block contains aggregates which interfere with the visual examination of the basidiospore placement.

The petri dish containing the C.S.A. blocks and basidiospore was then removed from the microscope, replacing the lid on the dish. A series of 25 such basidiospores were collected. After collection of all 25 basidiospores the C.S.A. block was removed with a small, flame sterilized, spatula and placed, each one individually, in the center of a 100 mm×15 mm sterile plastic petri dish containing C.S.A. at depth of about 5 mm. These petri dishes containing the basidiospores were then placed in plastic bags and incubated at 25° C. for 28 days. Nine cultures from the 25 basidiospore petri dishes were selected based upon the vigor of growth. These 9 cultures were arbitrarily numbered 1 through 9.

The 9 cultures were mated in every combination with each other. The procedure used for mating follows: Using standard sterile technique, a 21 ga tungsten inoculating needle with a 90' hook was used to remove eight small bits of culture. These bits were approximately 2 mm square containing intact mycelial growth covering the surface. Each of the 8 bits were placed onto a 100 mm×15 mm sterile plastic petri dish containing sterile C.S.A. Each bit was placed about 10 mm from the center and directly across from the similar bit from another of the 9 cultures. The two cultures on each dish were selected for mating with each other for all possible combinations resulting in 36 matings. The 36 petri dishes containing basidiospore matings were placed in plastic bags and incubated at 25° C. for 14 days. After 14 days the cultures grew in size so that the perimeters came in contact. The cultures which exhibited a line of no growth between the two cultures at the point of contact were considered to have the same mating type. The cultures which fused at this contact point were considered to have opposite mating types and successfully mated.

Five cultures which exhibited a vigorous growth characteristics and a clear positive mating reaction were selected and arbitrarily identified as M1 through M5. These mated cultures were considered to be diploid, arising from the mating of two haploid (tetroidal) basidiospores. The five mated cultures were then removed from the petri dishes used in the mating procedure. The inoculum of the mated cultures was removed from the perimeter of the subsequent culture arising from the contact point of the monosporeus cultures. These cultures were transferred to culture tubes on C.S.A. and maintained using standard cultural practices.

The five cultures were evaluated for desirable carpophore morphology and production characteristics. Cultures M1, M2, M4 and M5 all produced expected production values as compared to the parent vegetative selection culture. Culture M4 however was slower to produce primoidia by 1 and 2 days in two of the three production trials. Culture M3 produced only a few carpophores and was possibly an error in identity of a positive mating reaction. The morphology of all the cultures evaluated was identical to the parent vegetative selection. For the purpose of conformity within the laboratory the three cultures M1, M2 and M5 were renumber for identification purposes as P14a, P14b and P14c respectively. The culture arising from M5 now identified as P14c is submitted as the culture for this patent application. The attached photograph represents mycelial culture, primordial carpophores and mature carpophores of various sizes of the petitioned culture P14c at (2×) twice life size.

I claim:

1. A novel mushroom, *Pleurotus ostreatus* kummeri, substantially as shown and described.

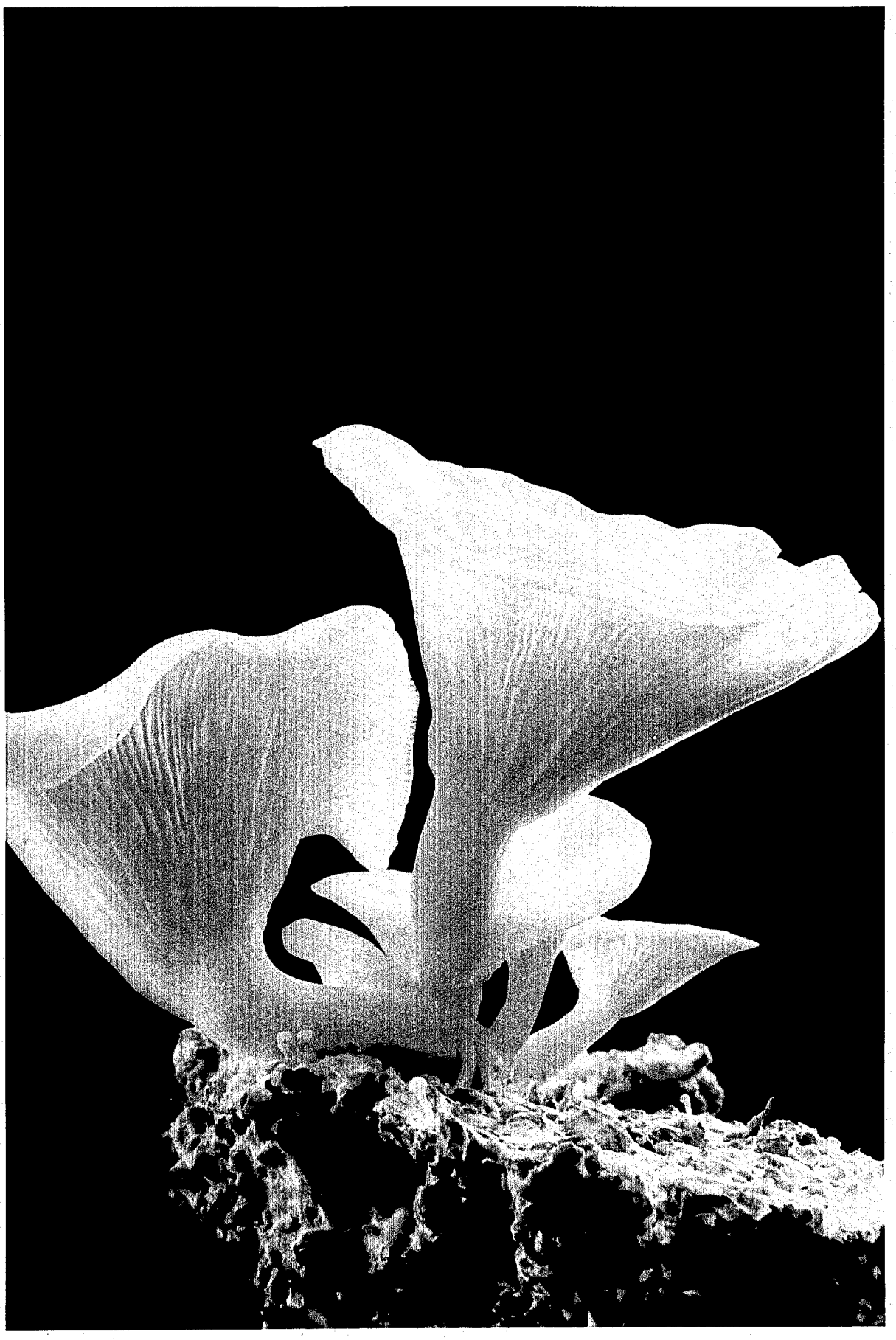

* * * * *